United States Patent [19]

Simpson

[11] Patent Number: 4,979,951
[45] Date of Patent: Dec. 25, 1990

[54] ATHERECTOMY DEVICE AND METHOD

[76] Inventor: John B. Simpson, 116 Fox Hollow Rd., Woodside, Calif. 94062

[21] Appl. No.: 298,846

[22] Filed: Jan. 18, 1989

Related U.S. Application Data

[63] Continuation of Ser. No. 132,675, Dec. 14, 1987, abandoned, which is a continuation of Ser. No. 732,691, May 10, 1985, abandoned, which is a continuation-in-part of Ser. No. 615,298, May 30, 1984, abandoned.

[51] Int. Cl.⁵ .............................................. A61B 17/32
[52] U.S. Cl. ................................... 606/159; 128/752; 128/755
[58] Field of Search .................... 128/751, 752, 755; 604/101, 96; 606/159

[56] References Cited

U.S. PATENT DOCUMENTS

| | | |
|---|---|---|
| 1,167,014 | 1/1916 | O'Brien . |
| 1,677,209 | 7/1928 | Rose . |
| 2,816,552 | 12/1957 | Hoffman . |
| 3,173,414 | 3/1965 | Guillant ............................ 128/305 |
| 3,435,826 | 4/1969 | Fogarty . |
| 3,704,711 | 12/1972 | Park ................................. 128/305 |
| 3,749,085 | 7/1973 | Willson et al. . |
| 3,811,448 | 5/1974 | Morton . |
| 3,990,453 | 11/1976 | Douvas . |
| 4,020,847 | 5/1977 | Clark, III . |
| 4,040,413 | 8/1977 | Ohshiro .............................. 128/6 |
| 4,137,920 | 2/1979 | Bonnet .............................. 128/305 |
| 4,220,155 | 9/1980 | Kimberling et al. . |
| 4,246,902 | 1/1981 | Martinez . |
| 4,273,128 | 6/1981 | Lary . |
| 4,274,414 | 6/1981 | Johnson et al. ..................... 128/305 |
| 4,295,464 | 10/1981 | Shihata . |
| 4,445,892 | 5/1984 | Hussein et al. ..................... 604/101 |
| 4,448,195 | 5/1984 | LeVeen et al. . |
| 4,493,321 | 1/1985 | Leather . |
| 4,627,436 | 12/1986 | Leckroni ......................... 128/303.1 |
| 4,685,458 | 8/1987 | Leckrone . |

FOREIGN PATENT DOCUMENTS

| | | |
|---|---|---|
| 0086048 | 8/1983 | European Pat. Off. . |
| 2453058 | 5/1976 | Fed. Rep. of Germany ...... 128/751 |
| 1161400 | 4/1958 | France . |
| 67204 | 6/1969 | German Democratic Rep. .................................. 128/751 |
| WO82/00408 | 2/1982 | PCT Int'l Appl. . |
| WO82/00592 | 3/1982 | PCT Int'l Appl. . |
| 2044103 A | 10/1980 | United Kingdom . |

Primary Examiner—Henry A. Bennet

[57] ABSTRACT

Atherectomy device having a generally cylindrical housing formed of a relatively rigid material. The housing has rounded distal and proximal end portions. The housing is formed with a cutout extending longitudinally of the housing on one side of the housing. An atheroma cutter is disposed to the proximal end of the housing and is used for advancing the housing into the arterial passage. A flexible drive cable extends through the flexible guide and is connected to the atheroma cutter for operation of the atheroma cutter.

60 Claims, 4 Drawing Sheets

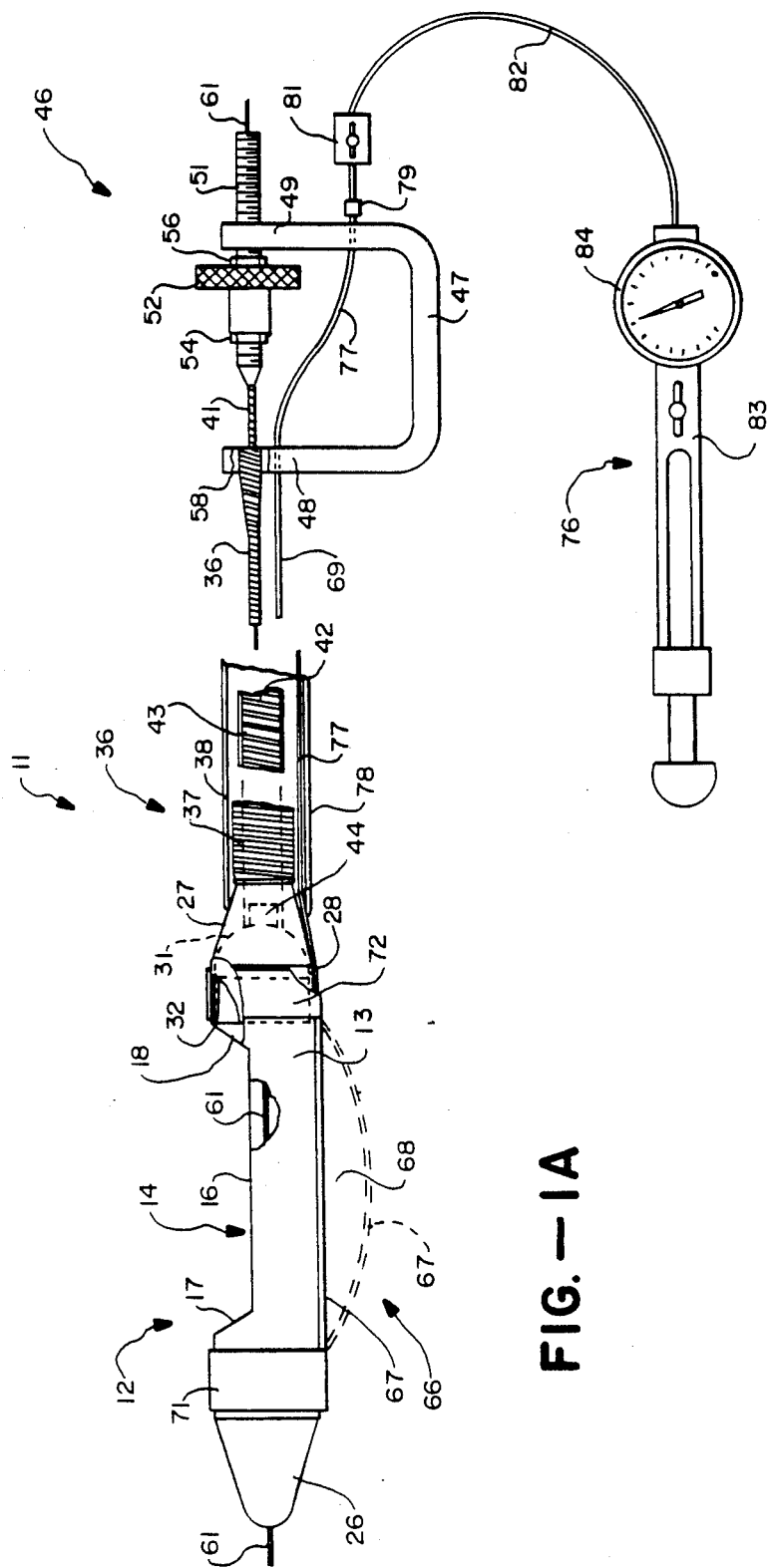

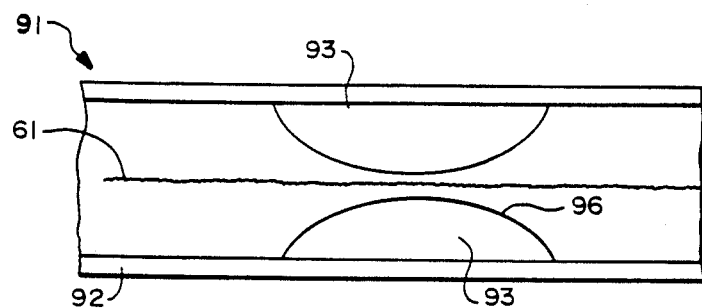
FIG.—2A
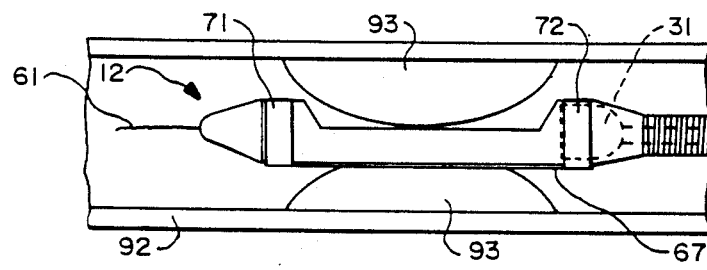
FIG.—2B
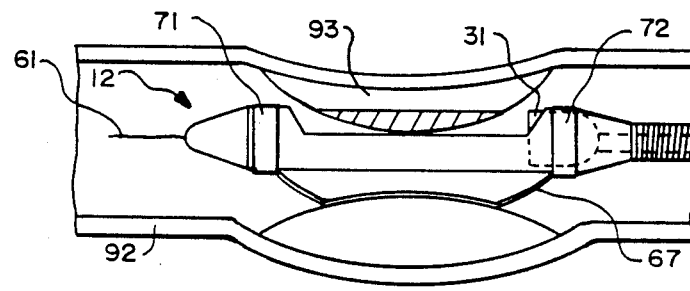
FIG.—2C
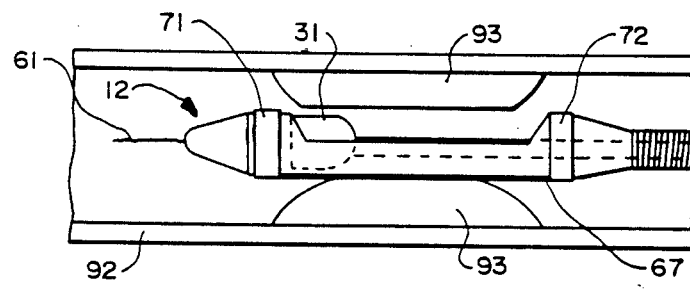
FIG.—2D
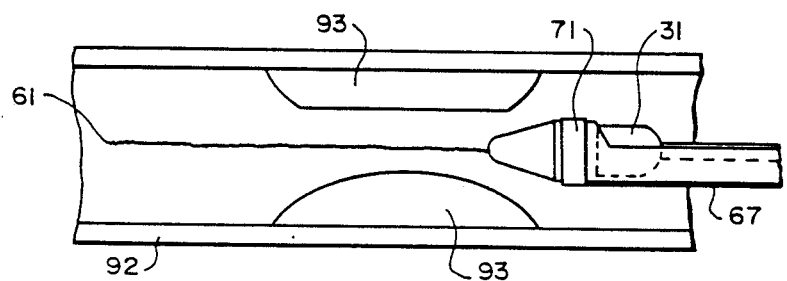
FIG.-2E

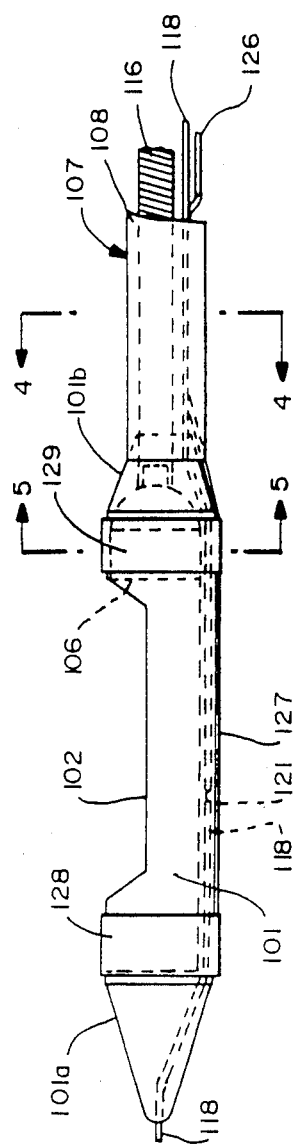
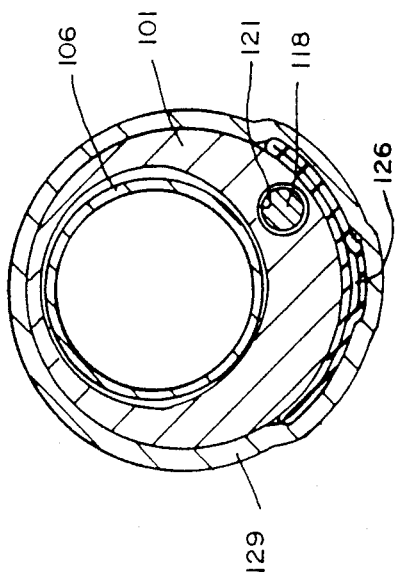
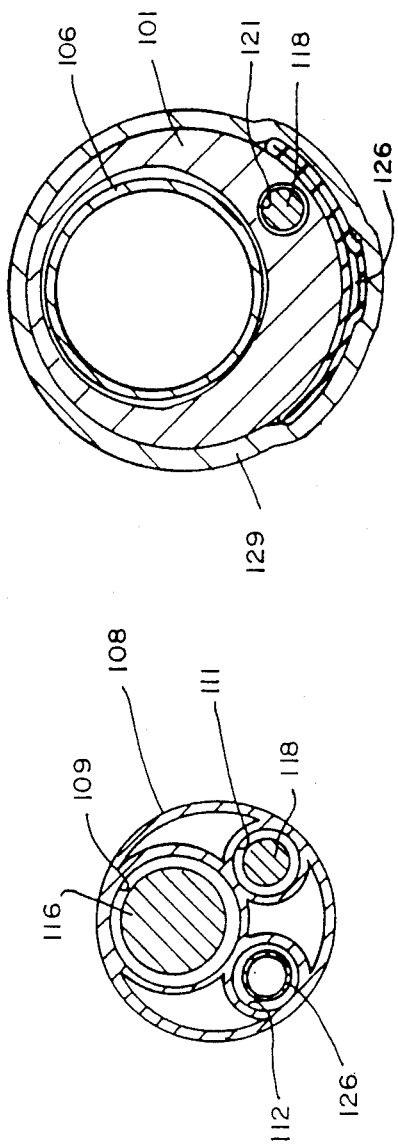

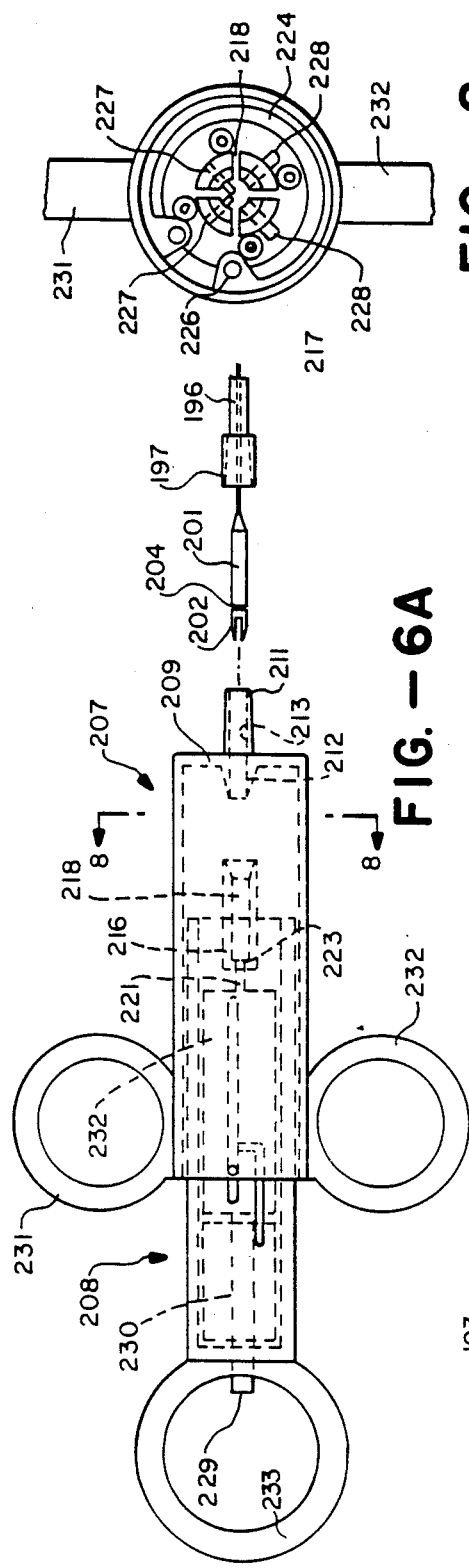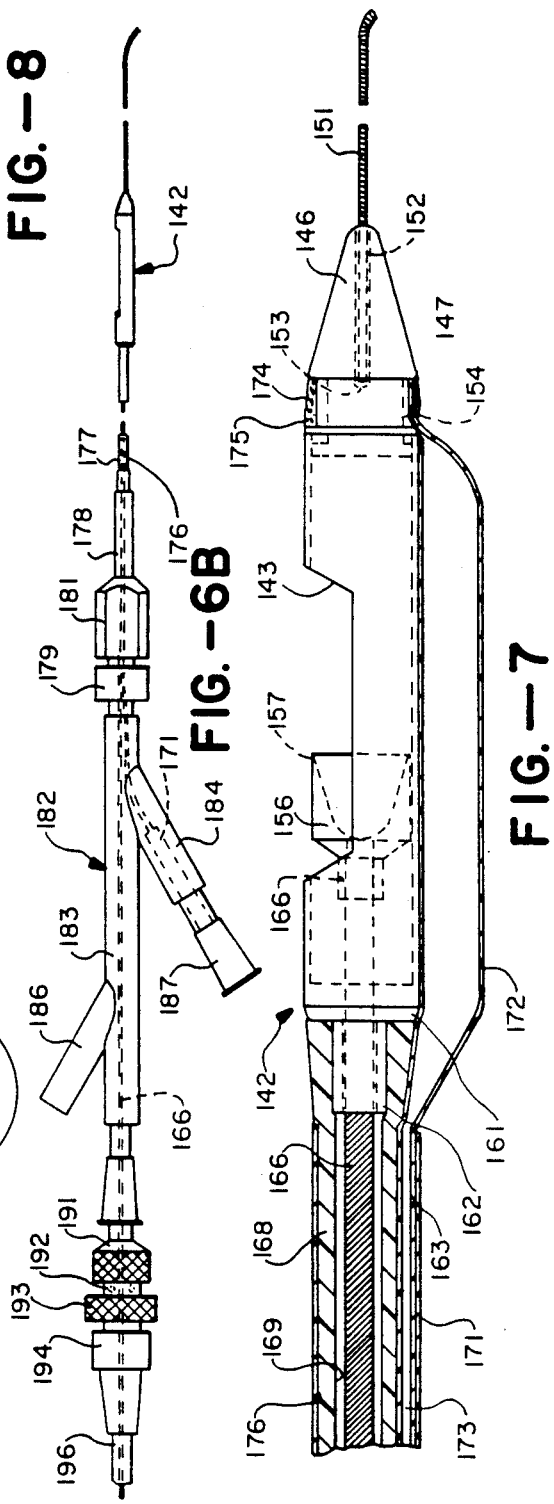

ATHERECTOMY DEVICE AND METHOD

This is a continuation of 07/132,675 filed Dec. 14, 1987 now abandoned which is a continuation of application Ser. No. 732,691 filed May 10, 1985 now abandoned which is a continuation of 06/615,298 filed 05/30/84 now abandoned.

This invention relates to an atherectomy device and a method for removing or minimizing atheromas and for taking biopsies.

Peripheral vascular arteriosclerosis is a common ailment occurring in humans which involves the deposition of a fatty-like substance called atheromas or plaque in blood vessels and particularly in the peripheral blood vessels that feed the limbs of the human body. Occasionally these fatty deposits occur in fairly localized regions in the blood vessel. Substantial success has been obtained in increasing the size of the flow passages in the arteries in which these deposits have occurred by the use of a dilitation process using balloon angioplasty. However, it has been found that in a substantial percentage as, for example, 20 to 30% of the cases which are treated in this manner there is a tendency for the atheromas to reoccur. There is a need for a device and a method which will substantially reduce such reoccurrences and thereby eliminate the need for additional dilitations.

In general, it is an object of the present invention to provide an atherectomy device and method by which atheromas in arteries can be at least partially removed or minimized.

Another object of the invention is to provide a device and method of the above character which can be utilized for taking biopsies.

Another object of the invention is to provide a device and method of the above character which is safe and efficacious.

Another object of the invention is to provide a device and method of the above character in which the cutting device is rotated rapidly while it is being advanced.

Another object of the invention is to provide a device and method of the above character in which the rotating motion of the cutter is motorized.

Another object of the invention is to provide a device and method of the above character in which the rotation and the advancement of the cutting device can be accomplished during motorized rotation.

Another embodiment of the atherectomy device is shown in FIGS. 6A and 6B and in FIGS. 7 and 8. As shown therein, the atherectomy device 141 consists of a housing 142. The housing 142 is formed of a suitable material such as stainless steel and has a generally cylindrical configuration. The housing 142 consists of a cylinder 143 and is provided with a cut-out 144 extending longitudinally of the same. The cut-out 144 is shaped Another object of the invention is to provide a device and method of the above character which can be readily inserted into arteries and particularly the peripheral blood vessels.

Another object of the invention is to provide a device of the above character which can be operated with ease.

Another object of the invention is to provide a device of the above character which can be readily manufactured.

Additional objects and features of the invention will appear from the following description in which the preferred embodiments are set forth in conjunction with the accompanying drawing.

FIGS. 1A and 1B are side elevational views with certain portions broken away of an atherectomy device incorporating the present invention in which FIG. 1A typically is approximately on a 10 to 1 scale and FIG. 1B, except for the inflating device, typically is approximately on a 1 to 2 scale.

FIGS. 2A through 2E show the method of the present invention in which the atherectomy device shown in FIG. 1 is utilized.

FIG. 3 is a partial side elevational view with certain portions broken away of another embodiment of the atherectomy device incorporating the present invention.

FIG. 4 is a cross section view taken along the line of 4—4 of FIG. 3.

FIG. 5 is a cross section view taken along the line 5—5 of FIG. 3.

FIGS. 6A and 6B show another embodiment of an atherectomy device incorporating the present invention in which the advancement and rotation of the cutter is motorized.

FIG. 7 is an enlarged detail view of the distal extremity of the atherectomy device shown in FIG. 6A and 6B.

FIG. 8 is an enlarged cross sectional view taken along the line 8—8 of FIG. 6A.

In general, the atherectomy device is comprised of a generally cylindrical housing formed of a relatively rigid material. The housing has rounded distal and proximal end portions. The housing is formed with a cutout extending longitudinally of the housing. Atheroma cutting means is disposed within the housing. Flexible guide means is secured to the proximal end of the housing for advancing the housing into the arterial vessel. Flexible drive means extends through the flexible guide means and is connected to the atheroma cutting means in the housing for causing operation of the atheroma cutting means to remove at least a portion of an atheroma from the arterial vessel.

More particularly the atherectomy device 11 as shown in FIGS. 1A and 1B of the drawings consists of a housing 12 which has a generally cylindrical configuration. The housing 12 can be formed of any suitable relatively rigid materials as, for example, stainless steel. However, if desired a rigid plastic can be utilized, particularly if the device is to be disposable. The housing 12 consists of a cylinder 13 having a suitable diameter as, for example, ranging from 0.030" to 0.150". The cylinder 13 is open-ended and is provided with a cutout 14 extending longitudinally of the same. The cutout 14 is formed so that the remaining portion of the cylinder in the vicinity of the cutout forms substantially a semi-cylinder. The cutout is defined by planar surfaces 17 of the sidewall of the cylinder lying in a plane parallel to the longitudinal axis of the cylinder 13 and upwardly and outwardly inclined end surfaces 17 and 18 adjoining opposite ends of the surfaces 17.

The housing 12 is provided with rounded end portions to facilitate movement of the housing within the coronary arteries. Thus on the distal extremity of the housing 12, there is provided a generally conical member 26 which is provided with a rounded extremity. The conical member 26 also is formed of a suitable material such as stainless steel or plastic. As shown the member 26 can be formed integral with the housing 12. Alternatively, it can be secured to the cylinder 13 by suitable means such as laser welding or a suitable adhesive.

A separate conical member 27 is secured to the proximal end of the cylinder 13. The proximal end of the cylinder 13 is provided with an annular recess 28 which is adapted to receive the conical member 27 and secured to the cylinder 13 by suitable means such as laser welding or by an adhesive. The housing 12 when so constructed has a smooth outer surface. The conical member 27 is truncated as shown.

Atheroma cutting means 31 is disposed within the housing 12. The cutting means 31 is cup-shaped as shown and is sized in such a manner so that it can fit into the cylinder 13 of the housing 12 and can be slidably moved longitudinally of the housing as hereinafter described. The cup-shaped cutting member 31 is provided with a circular continuous cutting edge 32 which lies in a plane perpendicular to the longitudinal axis of the housing 12. However, it should be appreciated that if desired the cutting edge can have other configurations. For example, the cutting edge can be inclined to form an elipse. Also the cutting edge can be undulating if desired. The atheroma cutting means is inserted into the housing 12 before the conical member 27 is secured to the cylinder 13.

Flexible guiding means 36 is secured to the proximal extremity of the housing 12. The flexible guiding means 36 is in the form of an elongate hollow cylindrical cable-like member or coil spring 37 formed of a suitable material such as stainless steel. The cable-like member or spring 37 is covered with a tubular member 38 of suitable material such as a heat shrinkable plastic to prevent the coils of the cable-like member or spring from separating and also to enhance the type of control which can be provided by the cable-like member or spring so that the housing 12 and the flexible guiding means 36 can follow different curves in the blood vessels and tortuous segments of blood vessels. The flexible guiding means 36 can be secured to the truncated end of the conical member 27 by suitable means such as welding or an adhesive.

Flexible drive means 41 is provided for operating the cutting means 31 and is also formed of an elongate cylindrical cable-like member or coil spring 42 of a suitable material such as stainless steel and in which the cable-like member o spring 42 is covered with a tubular member 43 of suitable material such as a heat shrinkable plastic to prevent separation of the coils of the spring or cable 42 and also to facilitate movement of the flexible drive means 41 through the flexible guiding means 36. The flexible drive means 41 is secured to the proximal extremity of the atheroma cutting means 31 as shown particularly in FIG. 1 by welding or brazing the spring onto a stud 44 forming a part of the cutting means 31. In certain applications it may be desirable to use a plastic tube formed of a suitable plastic such as Teflon in place of the cable-like members used in the flexible guiding means 36 and the flexible drive means 41. Such a tube has been found to supply the necessary torsional strength.

Control means 46 is provided for controlling the movement of the housing 12 and operation of the cutting means 31 and for providing relative rotational movement between the same and movement of the cutting means 31 longitudinally of the axis of the housing 12. Such control means consists of a U-shaped control handle 47. The control handle is provided with spaced parallel legs 48 and 49. A threaded rod 51 is threaded into the leg 49 and extends in a direction at right angles to the leg 49. A knurled thumb screw 52 is rotatably mounted on the threaded rod 51 and is movable longitudinally of the rod and can be locked in a predetermined position by two lock nuts 54 and 56 adjustably positioned on the rod 51. The proximal extremity of the flexible guiding means 36 is mounted in a hole 58 provided in the leg 48 and is secured therein by a suitable means such as an adhesive. The flexible drive means 41 extends through the flexible guiding means 36 and has its proximal extremity secured to the tapered forward extremity of the threaded rod 51 by suitable means such as an epoxy. The knurled knob is positioned so that when the lock nut 56 is adjacent the leg 49, the cutting means 31 is in its rearmost extremity and when the lock nut 54 is in a position engaging the other leg 48, the cutting means 31 is in its forwardmost position. This ensures that the spring which serves as the flexible drive means 41 is not stressed unduly.

A guide wire of conventional construction 61 is provided which extends through a bore (not shown) provided in the threaded rod 51 and through the interior of the flexible drive means 41 and thence through the cutting means 31, through the housing 12 and through the conical member 26 of the housing 12.

Inflatable means 66 is provided for moving the housing 12 after it has been advanced into the desired position in the arterial vessel into close proximity to the atheroma on which a cutting operation is to be performed. The inflatable means 66 is carried by the housing 12 exterior of the housing 12 in a region opposite the cutout 14. This inflatable means 66 takes the form of a balloon 67 formed in a conventional manner integral with and at the end of an elongate tubular member 69 formed of plastic. The balloon can be very thin walled and need only take pressures typically in a range from 20 to 30 psi. The balloon 67 preferably extends the length of the cylinder 13 and is secured to the exterior surface of the housing 12 at opposite ends of the cylinder 13 by suitable means such as bands 71 and 72 formed of a heat shrinkable plastic.

Inflating means 76 is provided for supplying a fluid to the balloon 67 and includes the flexible tubular member 77 which provides a lumen which opens into the balloon 67. The member 77 extends along the flexible guiding means 36 to the the control handle 47. It can be held in close proximity to the guiding means 36 by another heat shrinkable tubular member 78. The tubular member 77 is provided with a suitable fitting as, for example, a Luer adapter 79 which is adapted to be connected to suitable valve means as, for example, a two-way stop cock 81. The stop cock 81 is connected by a tube 82 to a balloon inflating device 83 called an "Indeflator" and described in U.S. Letters Pat. No. 4,439,185. The Indeflator is used for introducing a fluid into the tubular member and to inflate the space 68 in the balloon 67 so that its outer side wall assumes the position represented. The pressure applied to inflate the balloon is observed by reading the gauge 84.

It should be appreciated that the tubular member 77, if desired, can be positioned within the flexible guiding means 36. Also, the U-shaped control handle 47 can be provided with openings or holes (not shown) in the arms 48 and 49 which can receive the tubular member 77.

Operation of the atherectomy device shown in FIGS. 1B and 1B may now be briefly described in conjunction with the method of the present invention as shown in FIGS. 2A to 2E. Let it be assumed that it is desired to cut out at least a portion of an atheroma in an arterial vessel. The arterial vessel 91 shown in FIG. 2A has a wall 92 which has an atheroma 93 formed thereon. Let it also be assumed that it is desired to cut out at least a portion of the atheroma 93 in the arterial vessel 91. To accomplish this, an incision is made in the human body to make it possible to enter the arterial vessel in which the atheroma 93 is located. The distal tip of the guide wire 61 is inserted into the arterial vessel and advanced in the vessel until it extends through the arterial vessel through the stenosis, or narrowing 96 of the vessel created by the atheroma as shown in FIG. 2A. Thereafter the proximal end of the guide wire 61 is threaded through atherectomy device 11 by inserting the guide wire 61 through the housing 12, the guiding means 36 and the threaded rod 51.

At this point in the operation, the cutting means 31 is completely retracted in the housing 12 to the position shown in FIG. 1A of the drawings. The atherectomy device 11 is then inserted into the arterial vessel with the housing 12 going first. The flexible guiding means 36 provided for the housing 12 makes it possible for the atherectomy device to enter readily the arterial vessel and to follow the lumen in the arterial vessel. To facilitate advancement of the housing 12, the control handle 47 can be rotated back and forth. Advancement is continued until the housing 12 is positioned in the vicinity of the atheroma 93 as shown in FIG. 2B. The positioning of the housing 12 can be observed by the use of a fluoroscope. The housing 12 as hereinbefore explained can be made of a material such as stainless steel which is relatively opaque to X-rays and thus gives a good image as the device is being positioned in the arterial vessel.

After the housing 12 is properly positioned as shown in FIG. 2B, the balloon 67 is inflated by use of the inflating means 76 to force the housing 12 firmly into engagement with the atheroma 93 and particularly so that a substantial portion of the atheroma is positioned in the cutout 14. The inflation is accomplished by opening the stop cock 81 and introducing a fluid by operation of the Indeflator 83. The pressure at which the fluid is introduced into the balloon ca be readily observed by reading the gauge 84 of the Indeflator 83. The balloon can be inflated with a saline solution or even air if desired since only a relatively low pressure is required, as for example, 20 to 30 psi. The inflation pressure is substantially less than that used for dilitation because the purpose is merely to position the housing 12 so it is in a snug position against the atheroma.

The balloon 67 when inflated engages the opposite side of the atheroma received by the cutout 14. As seen, the balloon 67 when inflated can accommodate the configuration of the atheroma 93 and thus apply a desired equalizing pressure to urge the housing towards the atheroma in the manner shown in FIG. 2C. As this is occurring it has been found that the vessel wall 92 bulges outwardly below the balloon and bulges inwardly on the opposite side so that the atheroma is depressed into the cutout 14 of the housing 12 as shown in FIG. 2C.

The cutting means 11 may now be operated. This is accomplished by rotating the thumb screw 52. As the thumb screw 52 is rotated as, for example, in a clockwise direction, the threaded rod 51 upon which the thumb screw 52 is mounted is rotated in the arm 47 so that the thumb screw 52 is advanced. This movement of thumb screw 52 causes rotation and advancement of the flexible drive means 41 which causes rotation and advancement of the cutting means 31. It should be appreciated that either or both the flexible guiding means 36 or the flexible drive means 41 can be rotated in opposite directions to cause this rotation with longitudinal advancement. The inflated balloon 67 serves to maintain the housing in engagement with the atheroma 93 so that it will not be pushed away from the atheroma 93 as the cutting means 31 engages the atheroma. This operation continues until the cutting edge 33 engages the atheroma and begins cutting the portion of the atheroma within the cutout 14 to remove the portion which is shown as cross hatched in FIG. 2C. As the cross hatched portion is removed in the cutting operation in the manner shown in FIG. 2D it is collected within the cup-shaped cutting means 31 and advanced into the forward conical-shaped extremity of the housing 12. The inflated balloon 67 serves to ensure that the atheroma 93 remains in the cutout during operation of the cutting means 31.

Thereafter, the entire atherectomy device 11 can be removed from the arterial vessel as shown in FIG. 2E taking with it the portion of the atheroma which has been severed. After the device has been removed from the arterial vessel, the material collected within the housing 12 is removed. In removing the atherectomy device, the guide wire can be left in place so that multiple cutting operations can be performed if necessary to remove sufficient material from the atheroma. If multiple cutting operations are to be performed on the same atheroma, the device can be removed after each cutting operation and cleaned. Additional portions of the atheroma can be removed with additional passes of the cutting means 31 until a sufficiently large passage is established to ensure that there is very little likelihood of any further possibility of occlusion of the blood vessel.

It should be appreciated that if desired, the housing 12 can be increased in length to store additional material cut from the atheroma. Also, the housing can be formed of flexible material so that it can expand as more material is deposited from the cutting device.

Another embodiment of the atherectomy is a device is shown in FIGS. 3 through 5. As shown therein, it also consist of a cylindrical housing 101 which is formed of plastic and which is provided with an elongate cutout 102 similarly to the cutout 14 hereinbefore described. The distal extremity of the housing is provided with a rounded portion 101a and similarly the proximal extremity of the housing 101 is provided with a rounded portion 101b. This rounded portion 101b can be formed as a separate part and bonded to the main body of the housing 101 by suitable means such as an adhesive after the atheroma cutting means or cutter 106 has been mounted within the cylindrical housing. The cutter 106 can be identical to the atheroma cutting means 31 hereinbefore described and is movable longitudinally of the housing 101.

Flexible guiding means 107 is secured to the proximal extremity of the conical portion 101b of the housing 101 and consists of a flexible plastic tube 108. The tube 108, as shown, can be formed as an extruded member which is provided with three separate lumens 109, 111, and 112.

Flexible drive means in the form of a cable 116 is provided for driving the cutter 106. The cable 116 can be hollow or solid. It is shown as being solid in FIG. 4 and is disposed in the large lumen 109 provided in the tube 108. The distal extremity of the flexible cable 116 can be secured to the cutter 106 by a suitable means such as an adhesive. The flexible tube 108 can be secured to the leg 48 of the U-shaped member 47 in the same manner that the guiding cable 36 is secured thereto. Similarly, the drive cable 116 can be secured to the knob 52 in the same manner that the flexible drive means 41 is secured to the knob 52. A flexible guide wire 118 is provided which extends through the lumen 111. The lumen 111 is in communication with a passageway 121 which is provided in the plastic housing 101. The passageway 121 extends the length of the housing 101 and curves up towards the distal extremity of the same so that the passage 121 exits centrally of the housing 101. As can be seen, the guide wire 118 extends through this passageway 121 and exits through the rounded portion 101a so that it can be utilized for guiding the housing 101 in its travel through the arterial blood vessel.

A balloon tube 126 extends through the lumen 112 and is provided with an integral inflatable balloon 127 of the same type as balloon 67. The inflatable balloon 127 is secured to the housing 101 by plastic bands 128 and 129.

The proximal extremities of the guide wire 118 and the balloon tube 126 can be brought out at the proximal extremity of tube 108 adjacent the U-shaped member 47. The balloon tube 126 can be connected to an inflating device such as device 76 as shown in FIG. 1B. The guide wire 118 can be manipulated in a conventional manner.

Operation of this embodiment of the atherectomy device shown in FIGS. 3 through 5 may now be briefly described as follows. The operation of the device is very similar to that hereinbefore described with respect to the embodiment as shown in FIGS. 1A and 1B. The principal difference between the two embodiments is that the guide wire 118 need not pass through the cutter 106 or through the center of the housing, as is the case, in the embodiment shown in FIGS. 1A and 1B. Rather, as shown, the guide wire is introduced through the housing through a passageway 121 provided in the housing. This makes it possible to insert and remove the guide wire 118 from the atherectomy device even though material may already have been cut by the cutter 106 and be disposed within the housing 101.

Another embodiment of the atherectomy device is shown in FIGS. 6A and 6B and in FIGS. 7 and 8. As shown therein, the atherectomy device 141 consists of a housing 142. The housing 142 is formed of a suitable material such as stainless steel and has a generally cylindrical configuration. The housing 142 consists of a cylinder 143 and is provided with a cut-out 144 extending longitudinally of the same. The cut-out 144 is shaped in a manner similar to the cut-out 14 in the embodiment of the atherectomy device shown in FIGS. 1A and 1B. A conical nose piece 146 is provided which is fitted into the distal extremity of the cylinder 143 by a suitable means such as an adhesive. An annular recess 147 is provided adjacent the distal extremity of the cylinder 143 for a purpose hereinafter described. A guide wire 151 is mounted in the nose piece 146 and extends forwardly therefrom. It has its proximal extremity positioned in a bore 152 provided in the nose piece and is soldered into the nose piece at 153 within a cylindrical recess 154 provided in the proximal extremity of the nose piece. The guide wire 151 can be of any suitable type such as a coil spring 151 formed of a radiopaque material such as tungsten.

Cutting means in the form of a cutter 156 is provided in the housing 142. The cutter 156 is similar to the cutter 31 shown in FIG. 1A. It is cup shaped and is provided with a continuous circular cutting edge 157. A tail piece 161 is mounted in the proximal extremity of the cylinder 143 and is secured therein by suitable means such as an adhesive. The tail piece 161 is provided with a rearwardly extending boss 162. The last piece 161 is provied with a bore 163 extending therethrough. Means is provided for rotating and advancing the cutter 156 and consists of a torque cable 166. The distal extremity of the torque cable 166 extends through the bore 163 and is secured to a boss 167 provided as a part of the cutter 156 by suitable means such as an adhesive. The torque cable 166 is housed in a torque tube 168 which is fitted over the proximal extremity of the tail piece 161 as shown particularly in FIG. 7. The torque tube 168 can be formed of any suitable material such as plastic. A lumen 169 is formed in the torque tube through which the torque cable 166 passes and through which a radiocontrast liquid can pass as hereinafter described.

A balloon tube 171 is provided which lies adjacent to the torque tube 168. The balloon tube 171 has a balloon 172 formed integral therewith on the distal extremity of the same. The balloon tube 171 has a lumen 173 which extends through the same which is in communication with the interior of the balloon 172 so that the balloon 172 can be inflated and deflated as hereinafter described. The distal extremity of the balloon 172 is secured to the nose piece 146 in the recess 154 by a suture 174 formed of a suitable material such as Nylon wrapped about the distal extremity of the balloon in the recess 154. This suture 174 is potted in a urethane compound 175 so as to provide a smooth surface and a smooth transition between the outer cylindrical surface of the cylinder 143 and the conical nose piece 146.

A third tube 176 is provided which encloses both the torque tube 168 and the balloon tube 171 and can be formed of a suitable material such as a heat shrinkable plastic so that the three tubes are tightly encased into a unitary assembly. The distal extremity of the tube 176 serves to retain the proximal extremity of the balloon 172 in tight engagement with the proximal extremity of the housing 142 so that the balloon will only be formed along the length of the housing 142 to the rear of the conical nose piece 146 and underlying the cutout 143.

In order that the atherectomy device 141 can be readily introduced into the vessels of the patient, the tube 176 can be coated with a lubricious material such as MDX supplied by Dow Corning which is essentially a silicone-based coating or alternatively, a Teflon-type coating such as DuPont Vydex. In addition, in order to provide a very smooth and still relatively hard surface, the stainless steel parts for the housing 142 can be coated with titanium nitride.

The proximal extremity of the tube 176 is secured to shrink tube sections 177 and 178 of progressively larger diameters. The tube section 178 is fitted over the distal extremity of a fitting 179 and is secured thereto by a cap 181 which is threaded onto the fitting 179. The fitting 179 is connected to a three-arm adapter 182 which is provided with a central arm 183 and two side arms 184 and 186. The balloon tube 171 extends through the three-arm adapter 182 and is connected to a fitting 187 mounted in the side arm 184. The fitting 184 is utilized for inflating and deflating the balloon. The side arm 186 is in communication with the lumen 169 provided in the torque tube 168 and can be utilized for injecting radiographic contrast fluid as hereinafter described.

The torque cable 166 also extends through the three arm adapter 182 and extends into a fitting 191 mounted on the central arm 183. The fitting 191 is provided with an O-ring through which the torque cable 166 passes and which is adapted to be pressed into engagement with the torque cable 166 to form a liquid-tight seal by the use of a thumb screw 193 threaded into the fitting 191. A fitting 194 is mounted on the thumb screw 193 and rotates with the thumb screw. A tube 196 has one end secured to the fitting 194 and has its other end secured to a fitting 197. The torque cable 166 extends through the tube 196 and through the fitting 197 and is secured to a first clutch member 201. The clutch member 201 has a generally cylindrical configuration and is provided with a pair of rearwardly extending ears 202 with a slot 203 therebetween. The clutch member 201 is provided with an annular recess 204.

Motive drive means is provided for engaging the clutch member 201 and for rotating the same and comprises a motor drive unit 206. The motor drive unit 206 consists of cylindrical members 207 and 208 with the cylindrical member 207 being an outer cylindrical member and the cylindrical member 208 being an inner cylindrical member with the inner cylindrical member telescoping within the outer cylindrical member 207 in much the same manner as a medical syringe. The cylindrical member 207 is provided with a distal wall 209 which has an outwardly extending centrally disposed tapered boss 211 and an inwardly extending tapered boss 212 through which a bore 213 is provided. The tapered boss 211 is formed so as to form a friction fit with respect to the fitting 197. The tapered boss 212 is adapted to be engaged by a second clutch member 216 which is adapted to mate with the first clutch member 201. The clutch member 216 is provided with a generally cylindrical recess 217 which is adapted to receive the first clutch member 201. The clutch member 216 is provided with four slits 218 spaced 90° apart. The second clutch member 216 is connected to an output shaft 221 of a small DC electric motor 222 by a set screw 223 of a conventional type. The motor 222 is mounted in the inner cylindrical member 208. The motor output shaft 221 rotates at a suitable speed as for example from 1,500 to 2,500 revolutions per minute. A DC power supply in the form of a cylindrical battery 223 is provided for energizing the motor 222. The battery 223 and the motor 222 are mounted in line within the cylindrical member 208 and are held in place by a sleeve 224 engaging the motor 222. The sleeve 224 is held in place by a C-clamp 226. A pair of pins 227 are mounted in the second clutch member 216 and extend into the recess 217 and are adapted to seat in the slot 203 of the first clutch member 201. An additional pair of pins 228 are provided in the clutch member 216 and are adapted to seat in the recess 204 of the clutch member 201. A hand operated switch 224 is also mounted on the proximal extremity of the cylindrical member 208 and has a spring contact which is adapted to engage one end of the battery 223 with the other end of the battery being in contact with a terminal of the motor 222. A lead 226 is provided for connecting the contact of the switch 224 to the other terminal of the motor 222.

Means is provided for grasping the motor drive unit 206 so that it can be held and operated by one hand. To this end there have been provided a pair of finger rings 231 and 232 which are mounted on the proximal extremity of the cylindrical member 207 diametrically opposite each other which are adapted to be engaged by two fingers of a hand. In addition there has been provided a circular finger member 233 which is mounted on the proximal extremity of the cylindrical member 208 and is adapted to be engaged by the thumb of the same hand which is utilized for the finger members 231 and 232. In this way, the motor drive unit 206 can be held by one hand with two fingers in the finger members 231 and 232 and the thumb in the finger member 233. The thumb can be used to operate the switch 224 to energize the motor 222. The motive drive means is provided with means permitting the cutter 156 to be advanced and retracted while it is being rotated and consists of a guide slot 236 provided on the outer wall of the cylindrical member 208 extending longitudinally of the same for a predetermined distance. The recess 236 is adapted to be engaged by a set screw 237 mounted in the side wall of the cylindrical member 207. This permits relative longitudinal movement of the cylindrical member 208 with respect to the member 207 between the extremities of the slot or recess 236. An additional slot 241 is provided adjacent and parallel to the slot 236. The slot 241, although shorter than slot 236, extends rearwardly of the cylindrical member 208 for a distance beyond that of the slot or recess 236. A transverse slot 242 is also provided which is in communication with the slots 236 and 241.

It can be seen that by rotating the cylindrical members 207 and 208 with respect to each other, the pin 237 can be moved into either the slot 241 or the slot 236 by use of the transverse slot 242. When the pin 237 is moved into the slot 241, the cylindrical member 208 can be moved forwardly into the cylindrical member 207 so that the second clutch member 216 engages the conically shaped boss 212 to spread apart the clutch member 218 to permit the first clutch member 201 to be inserted therein or to be removed therefrom. Let it be assumed that it is desired to insert the first clutch member 201 into the second clutch member 216. This can be accomplished merely by moving the cylindrical member 208 forwardly in the member 207 in the slot 241 so that the second clutch member 216 comes into engagement with the cylindrical boss 212 to spread apart the distal extremities of the second clutch member 216. The clutch member 201 can be then inserted into the second clutch member so that at least one of the pins 227 seats in the slot 203 and so that the pins 228 seat in the recess 204. The fitting 197 can then be pressed onto the boss 211. The cylindrical member 208 can then be retracted so that the second clutch member is no longer opened by the conical boss 212 permitting it to frictionally grip the second clutch member 201. Thereafter, the cylindrical member 208 can be rotated so that the pin 237 is moved into the slot 236. The atherectomy device is now ready for use.

The atherectomy device 141 which is shown in FIGS. 6A, 6B and 7 can be utilized much in the same manner as the atherectomy device hereinbefore described. However, it has been found that by providing a motorized drive, the cutting operation performed by the cutter 156 is much more predictable and permits removable of material from the vessel in a fashion as to leave surgically smooth margins in the area in which material has been removed. With the motor drive unit 206 for the atherectomy device, the cutting operation can be performed relatively rapidly. At the same time that the cutter 156 is rotated it can be advanced by hand through the desired distance. This distance is determined by the length of the slot 236. The separation of the slot 236 from the 241 ensures that the first and second clutch members will not automatically be disengaged. As explained previously, this can only be accomplished by moving the pin 237 into the slot 241.

It has been found that by driving the cutter 156 at high speeds as, for example, the 1,500 to 2,500 revolutions per minute heretofore mentioned that the cutting operation can be performed with great precision. It should be appreciated that during the time the atherectomy device 141 is being used, the cutter 156 can be moved back and forth merely by controlling the relative positions of the cylindrical members 208 and 207 with respect to each other while at the same time that the cutter is being rotated by operating the switch 224 to energize the motor 222. The desired control means can be provided for adjusting the speed of rotation of the motor. The entire procedure can be observed under an x-ray since the position of the cutter and its travel can be visually observed.

Typically, the atherectomy device can be inserted into the vessel of the patient until the cut-out 153 is in the desired position in the stenosis after which the cutter can be advanced. After the cutter has been advanced through its length of travel, the atherectomy device can be removed and the cutter emptied of the material which has been removed. The atherectomy device can again be inserted into the vessel and another cutting operation performed. If necessary, this procedure can be repeated to ensure that an adequate opening has been provided in the vessel. To ensure that a uniform opening has been provided in the vessel, the housing 142 can be rotated into different positions so that the cut-out 143 faces different areas of the stenosis so that a smooth passage is formed in the vessel in which the operation is being performed.

Typically in using the atherectomy device, a radiocontrast dye is introduced into the vessel to ascertain where the stenosis is located. After the stenosis is located, the atherectomy device can be inserted into the stenosis by the use of the guide wire 151. After it is positioned in the stenosis and the housing rotated into the desired position so that the cut-out 143 faces the narrowing in the vessel, the balloon 172 can be inflated by introducing an inflation medium through the fitting 187. Radiographic contrast fluid can be introduced through the side arm 186 so it can pass through the lumen 169 provided in the torque tube 168. The O-ring seal 192 provided prevents liquids from the vessel from leaking from the atherectomy device.

If there is a substantial narrowing in the stenosis, it will be necessary to repeat the procedure a number of times as, for example, from as many as 7 to 20 passes. Upon each successive pass the housing can be rotated by a certain number of degrees as, for example, 10 degrees. If desired, successive passes can be separated by as many as 90°.

The atherectomy device 141 can have housings of various sizes ranging from 12 French down to 4 and 5 French and possibly as low as a 3 French, even though at the smaller sizes the material removed by the device in each pass is quite small. However, even with such a small device it is believed that there are applications for the device in areas where very small diameter vessels are being surgically treated.

It is apparent from the foregoing that there has been provided an atherectomy device which is particularly efficacious in removing material from atheromas in arterial vessels. This is particularly advantageous in that it is less likely that such atheromas will reoccur after they have been removed surgically by the device of the present invention utilizing the present method.

What is claimed is:

1. An atherectomy device comprising:
   a flexible member having proximate and distal ends;
   a housing disposed at the distal end of the flexible member, said housing having a cutout extending longitudinally on one side thereof and having a length greater than the width of the housing;
   cutting means disposed within the housing;
   drive means for translating the cutting means relative to the housing so that said cutting means will move past the cutout in the housing; and
   means on the housing for urging the housing in the direction of the cutout when the housing is in a blood vessel.

2. An atherectomy device as in claim 1, wherein the means for urging the housing in the direction of the cutout comprises a balloon mounted externally on the housing at a position opposite the cutout and means for inflating the balloon.

3. An atherectomy device as in claim 1, wherein the cutting means includes an arcuate cutting edge and the means for translating includes means for simultaneously rotating the arcuate cutting edge as it is moved past the cutout.

4. An atherectomy device as in claim 3, wherein the arcuate cutting edge defines a continuous cutting edge.

5. An atherectomy device as in claim 3, wherein the means for translating and rotating the cutting means includes an elongate torque member extending from the proximate end of the flexible member to the cutting means.

6. An atherectomy device as in claim 5, wherein the means for translating and rotating includes a motor attached to a proximal end of the elongate torque member.

7. An atherectomy device as in claim 1, further comprising means on the housing for guiding the flexible member through a patient's vascular system.

8. An atherectomy device as in claim 7, wherein the guiding means on the housing comprises a fixed guide wire.

9. An atherectomy device as in claim 7, wherein the guiding means comprises an axial passage in the housing capable of receiving a guide wire therethrough.

10. An atherectomy device comprising:
    a flexible member having proximate and distal ends;
    a housing disposed at the distal end of the flexible member, said housing having a cutout extending longitudinally on one side thereof and having a length greater than the width of the housing;
    cutting means having an arcuate cutting edge disposed within the housing;
    means for longitudinally translating the cutting means relative to the housing so that said cutting means will move past the cutout in the housing; and
    means for rotating the cutting means while it is being longitudinally translated, whereby atheroma extending through the cutout into the housing may be severed.

11. An atherectomy device as in claim 10, wherein the rotating means includes a motor disposed at the proximal end of the flexible member and an elongate torque member coupling the motor to the cutting means.

12. An atherectomy device as in claim 11, wherein the motor can rotate the cutting means at from 1500 to 2500 revolutions per minute.

13. An atherectomy device as in claim 10, further comprising means on the housing for urging the housing in the direction of the cutout when the housing is in a blood vessel.

14. An atherectomy device as in claim 10, further comprising means on the housing for guiding the flexible member through a patient's vascular system.

15. An atherectomy device as in claim 14, wherein the guiding means comprises a fixed guide wire.

16. An atherectomy device as in claim 14, wherein the guiding means comprises an axial passage capable of receiving a guide wire therethrough.

17. An atherectomy device as in claim 10, wherein the arcuate cutting edge is a circle or an ellipse.

18. An atherectomy device comprising:
   a flexible member having proximate and distal ends;
   a housing disposed at the distal end of the flexible member, said housing having a cutout extending longitudinally on one side thereof and having a length greater than the width of the housing;
   cutting means disposed within the housing;
   drive means for translating the cutting means relative to the housing so that said cutting means will move past the cutout in the housing; and
   means on the housing for guiding the flexible member through a patient's vascular system.

19. An atherectomy device as in claim 18, wherein the means on the housing for guiding the flexible member is a fixed guide wire.

20. An atherectomy device as in claim 18, wherein the means on the housing for guiding the flexible member is an axial passage capable of receiving a guide wire.

21. An atherectomy device as in claim 18, further comprising means on the housing for urging the housing in the direction of the cutout when the housing is in a blood vessel.

22. An atherectomy device as in claim 18, wherein the cutting means includes an arcuate cutting edge and the means for translating includes means for simultaneously rotating the arcuate cutting edge as it is move past the cutout.

23. An atherectomy device as in claim 22, wherein the arcuate cutting edge defines a continuous cutting edge.

24. An atherectomy device as in claim 22, wherein the means for translating and rotating the cutting means includes an elongate torque member extending from the proximate end of the flexible member to the cutting means.

25. An atherectomy device as in claim 24, wherein the means for translating and rotating includes a motor attached to a proximal end of the elongate torque member.

26. An atherectomy device comprising:
   a flexible member having a proximate and distal ends and a lumen extending between said proximate and distal ends;
   a cylindrical housing disposed at the distal end of the flexible member, said housing having a cutout extending longitudinally on one side thereof and having a length greater than the diameter of the housing;
   an elongate torque member disposed within the lumen and extending from the proximal end of the flexible member in to the cylindrical housing;
   a cutter member having an arcuate cutting edge attached to a distal end of the flexible torque cable within the housing;
   means for axially translating a proximal end of the torque cable, whereby the cutter may be moved past the cutout in the cylindrical housing;
   a motor attached to the proximal end of the elongate torque member, whereby the cutter member may be rotated while it is being axially moved;
   means on the housing for urging the housing in the direction of the cutout when the housing is in a blood vessel; and
   means on the housing for guiding the flexible member through a patient's vascular system.

27. An atherectomy device as in claim 26, wherein the arcuate cutting edge defines a continuous cutting edge.

28. An atherectomy device as in claim 26, wherein the means for translating includes a pair of mutually reciprocable members, with one member attached to the flexible member and the other member attached to the elongate torque member, wherein the reciprocable members may be manually reciprocated with one hand.

29. An atherectomy device as in claim 26, wherein the motor is mounted within the reciprocable member attached to the elongate torque member.

30. An atherectomy device as in claim 26, wherein the means for urging the housing in the direction of the cutout comprises a balloon mounted externally on the housing at a position opposite the cutout and means for inflating the balloon.

31. An atherectomy device as in claim 26, wherein the means on the housing for guiding the flexible member is a fixed guide wire.

32. An atherectomy device as in claim 26, wherein the means on the housing for guiding the flexible member is an axial passage capable of receiving a guide wire.

33. A method for removing atheromic material from a blood vessel, said method comprising:
   (a) positioning a housing having a longitudinally extending cutout within the blood vessel proximate an atheroma, said cutout having a length greater than the width of the housing;
   (b) urging the cutout against the atheroma so that an elongate portion of the atheromic material enters the housing; and
   (c) translating a cutting blade past the cutout while the housing is held generally in place relative to the atheroma, whereby the elongate portion of the atheromic material is severed and captured within the housing.

34. A method as in claim 33, wherein the housing is positioned over a guide wire.

35. A method as in claim 33, wherein the housing is positioned using a fixed guide wire attached to the housing.

36. A method as in claim 33, wherein the cutout is urged against the atheroma by inflating a balloon secured to the housing on a side opposite the cutout.

37. A method as in claim 33, wherein the cutting blade is translated longitudinally across the cutout.

38. A method as in claim 37, wherein the cutting blade is arcuate and is rotated while it is translated longitudinally across the cutout.

39. A method as in claim 36, wherein the cutting blade is rotated at from about 1500 to 2500 revolutions per minute.

40. A method as in claim 39, wherein the blade is rotated by a motor.

41. A method as in claim 33, wherein steps (b) and (c) are repeated in order to remove additional portions of atheromic material.

42. A method as in claim 41, wherein steps (b) and (c) are repeated without removing the housing from the blood vessel.

43. A method as in claim 41, wherein the housing is repositioned between successive translations of the cutting blade.

44. A method for removing atheromic material from a blood vessel, said method comprising:
 (a) positioning a housing having a longitudinally-extending cutout within the blood vessel proximate an atheroma, said cutout having a length greater than the width of the housing;
 (b) urging the cutout against the atheroma so that an elongate portion of the atheromic material enters the housing; and
 (c) translating and rotating a cup-shaped blade past the cutout while the housing remains urged against the atheroma, whereby the elongate portion of the atheromic material is severed and collected within the housing and the likelihood of releasing severed atheromic material into the blood vessel is minimized.

45. A method as in claim 44, wherein the housing is positioned over a guide wire.

46. A method as in claim 44, wherein the housing is positioned using a fixed guide wire attached to the housing.

47. A method as in claim 44, wherein the cutout is urged against the atheroma by inflating a balloon secured to the housing on a side opposite the cutout.

48. A method as in claim 47, wherein the blade is rotated at from about 1500 to 2500 revolutions per minute.

49. A method as in claim 46, wherein the blades is rotated by a motor.

50. A method as in claim 44, wherein steps (b) and (c) are repeated in order to remove additional portions of atheromic material.

51. A method as in claim 50, wherein steps (b) and (c) are repeated without removing the housing from the blood vessel.

52. A method as in claim 50, wherein the housing is repositioned between successive translations of the cutting blade.

53. An atherectomy device comprising:
 a flexible member having proximate and distal ends;
 a housing disposed at the distal end of the flexible member, said housing having a cutout extending longitudinally on one side thereof, wherein the cutout has a length greater than the width of the housing and the remaining portion of the housing in the vicinity of the cutout forms substantially a semi-cylinder;
 cutting means having an arcuate cutting edge disposed within the housing;
 means for longitudinally translating the cutting means relative to the housing so that said cutting means will advance past the cutout in the housing; and
 means for rotating the cutting means while it is being longitudinally translated, whereby atheroma extending through the cutout into the housing may be severed.

54. An atherectomy device as in claim 53, wherein the rotating means includes a motor disposed at the proximal end of the flexible member and an elongate torque member coupling the motor to the cutting means.

55. An atherectomy device as in claim 54, wherein the motor can rotate the cutting means at from 1500 to 2500 revolutions per minute.

56. An atherectomy device as in claim 53, further comprising means on the housing for urging the housing in the direction of the cutout when the housing is in a blood vessel.

57. An atherectomy device as in claim 53, further comprising means on the housing for guiding the flexible member through a patient's vascular system.

58. An atherectomy device as in claim 57, wherein the guiding means comprises a fixed guide wire.

59. An atherectomy device as in claim 57, wherein the guiding means comprises an axial passage capable of receiving a guide wire therethrough.

60. An atherectomy device as in claim 53, wherein the arcuate cutting edge is a circle or an ellipse.

* * * * *